United States Patent
Yamaguchi et al.

(10) Patent No.: US 10,087,424 B2
(45) Date of Patent: Oct. 2, 2018

(54) METHOD FOR ADJUSTING EXPRESSION OF HYDROXYMETHYLGLUTARYL COA REDUCTASE USING BZIP-TYPE TRANSCRIPTION FACTOR, ISOPRENOID-PRODUCING PLANT INTO WHICH GENE ENCODED FOR BZIP-TYPE TRANSCRIPTION FACTOR IS INTRODUCED, AND METHOD FOR MANUFACTURING POLYISOPRENOID IN WHICH SAID PLANT IS USED

(71) Applicant: SUMITOMO RUBBER INDUSTRIES, LTD., Kobe-shi, Hyogo (JP)

(72) Inventors: Haruhiko Yamaguchi, Kobe (JP); Yukino Inoue, Kobe (JP); Satoshi Kuroda, Kobe (JP)

(73) Assignee: SUMITOMO RUBBER INDUSTRIES, LTD., Kobe-Shi, Hyogo (JP)

( * ) Notice: Subject to any disclaimer, the term of this patent is extended or adjusted under 35 U.S.C. 154(b) by 55 days.

(21) Appl. No.: 14/902,191

(22) PCT Filed: Jul. 7, 2014

(86) PCT No.: PCT/JP2014/068044
§ 371 (c)(1),
(2) Date: Dec. 30, 2015

(87) PCT Pub. No.: WO2015/008644
PCT Pub. Date: Jan. 22, 2015

(65) Prior Publication Data
US 2016/0251632 A1    Sep. 1, 2016

(30) Foreign Application Priority Data

Jul. 16, 2013  (JP) ................ 2013-147805

(51) Int. Cl.
*C12N 15/82* (2006.01)
*C12N 9/04* (2006.01)
*C12P 5/00* (2006.01)

(52) U.S. Cl.
CPC ....... *C12N 9/0006* (2013.01); *C12N 15/8216* (2013.01); *C12N 15/8237* (2013.01); *C12N 15/8243* (2013.01); *C12N 15/8257* (2013.01); *C12P 5/007* (2013.01); *C12Y 101/01034* (2013.01)

(58) Field of Classification Search
CPC .................................................. C12N 9/0006
See application file for complete search history.

(56) References Cited

U.S. PATENT DOCUMENTS

| 8,124,839 B2 * | 2/2012 | Park | G01N 33/5097 800/282 |
| 8,765,403 B2 * | 7/2014 | Dueber | C12N 15/1044 435/132 |
| 2007/0079401 A1 | 4/2007 | Lough et al. | |
| 2011/0008829 A1 * | 1/2011 | Dueber | C12N 15/1044 435/68.1 |

FOREIGN PATENT DOCUMENTS

| JP | 2000-50884 A | 2/2000 |
| JP | 2002-537834 A | 11/2002 |
| JP | 2003-525024 A | 8/2003 |
| JP | 2004-527265 A | 9/2004 |
| JP | 2008-500063 A | 1/2008 |
| JP | 2011-520471 A | 7/2011 |
| WO | WO 02/015675 A1 | 2/2002 |
| WO | WO 02/099095 A2 | 12/2002 |
| WO | WO 2006/133461 A1 | 12/2006 |
| WO | WO 2009/108774 A2 | 9/2009 |
| WO | WO 2011/140329 A1 | 11/2011 |
| WO | WO 2014/007285 A1 | 1/2014 |
| WO | WO 2014/054602 A1 | 4/2014 |

OTHER PUBLICATIONS

De Nigris et al. International Journal of Cardiology, 2002; vol. 86, pp. 153-168.*
Fricke, J. et al. Plant Cell Physiology, (2013), vol. 54, No. 4; pp. 448-464.*
Nigris et al. International Journal of Cardiology, 2002; vol. 86, pp. 153-168.*
Hanson et al., The Plant Journal (2008) vol. 53, pp. 935-949.*
Silveira, A.B. et al., Plant Science, 2007; vol. 172, pp. 1148-1156.*
Jozwiak, A. et al. Biochimica et Biophysica Acta, 2013; vol. 1831, pp. 438-447.*
Jakoby, M. Trends in Plant Science; Mar. 2002, vol. 7, No. 3: pp. 106-111.*
Bamba et al., "Mevalonate Pathway is Responsible for Polyisoprenoid Biosynthesis in Eucommia Ulmoides Oliver," Japanese Society for Chemical Regulation of Plants, vol. 37, pp. 29-30, Oct. 29, 2002.
Chaban et al., "The bZIP63 Transcription Factor: From Transcriptional Regulation to Functional Analysis," Plant Biology, 1 page, 2009.
De Nigris et al., "New Insights in the Transcriptional Activity and Coregulatory Molecules in the Arterial Wall," International Journal of Cardiology, vol. 86, pp. 153-168, 2002.

(Continued)

*Primary Examiner* — Russell Kallis
(74) *Attorney, Agent, or Firm* — Birch, Stewart, Kolasch & Birch LLP (57) ABSTRACT

The present invention provides a method enhancing the polyisoprenoid biosynthesis pathway. Also provided are an isoprenoid-producing plant having an overall enhanced pathway of polyisoprenoid biosynthesis, and a method of producing a polyisoprenoid using the isoprenoid-producing plant. The present invention relates to a method of regulating the expression of hydroxymethylglutaryl-CoA reductase by a bZIP transcription factor.

5 Claims, 1 Drawing Sheet
Specification includes a Sequence Listing.

(56) References Cited

OTHER PUBLICATIONS

Ehlert et al., "Two-Hybrid Protein-Protein Interaction Analysis in *Arabidopsis protoplasts*: Establishment of a Heterodimerization Map of Group C and Group S bZIP Transcription Factors," The Plant Journal, vol. 46, No. 5, pp. 890-900, 2006.

Hao et al., "Laticifer Differentiation in Hevea brasiliensis: Induction by Exogenous Jasmonic Acid and Linolenic Acid," Annals of Botany, vol. 85, pp. 37-43, 2000.

Jakoby et al., "bZIP Transcription Factors in *Arabidopsis*," TRENDS in Plant Science, vol. 7, No. 3, pp. 106-111, Mar. 2002.

Kang et al., "The *Arabidopsis* bZIP1 Transcription Factor Is Involved in Sugar Signaling, Protein Networking, and DNA Binding," Molecular Plant, vol. 3, No. 2, pp. 361-373, Mar. 2010.

Kera et al., "Identification and Characterization of a Cis,Trans-mixed Heptaprenyl Diphosphate Synthase from *Arabidopsis thaliana*," FEBS Journal, vol. 279, No. 20, pp. 3813-3827, 2012.

Kuzuyama, "Mevalonate and Nonmevalonate Pathways for the Biosynthesis of Isoprene Units," Bioscience, Biotechnology, and Biochemistry, vol. 66, No. 8, pp. 1619-1627, 2002.

Lara et al., "Synergistic Activation of Seed Storage Protein Gene Expression in *Arabidopsis* by ABI3 and Two bZIPs Related to OPAQUE2," The Journal of Biological Chemistry, vol. 278, No. 23, pp. 21003-21011, Jun. 6, 2003 (published online Mar. 25, 2003).

Maruyama et al., "ATF6α Stimulates Cholesterogenic Gene Expression and de Novo Cholesterol Synthesis," Bioscience, Biotechnology, and Biochemistry, vol. 77, No. 8, pp. 1734-1738, 2013 (published online Aug. 7, 2013).

Okada, "The Biosynthesis of Isoprenoids and the Mechanisms Regulating It in Plants," Bioscience, Biotechnology, and Biochemistry, vol. 75, No. 7, pp. 1219-1225, 2011 (published online Jul. 7, 2011).

Yang et al., "Metabolic Response of Mice to a Postnatal Ablation of CCAAT/Enhancer-binding Protein α," The Journal of Biological Chemistry, vol. 280, No. 46, pp. 38689-38699, Nov. 18, 2005 (published online Sep. 15, 2005).

\* cited by examiner

```
                          SEQUENCE LISTING

<160> NUMBER OF SEQ ID NOS: 13

<210> SEQ ID NO 1
<211> LENGTH: 834
<212> TYPE: DNA
<213> ORGANISM: Arabidopsis thaliana

<400> SEQUENCE: 1
atggataatc acacagctaa agacattggt atgaagagaa gtgcttctga gctggctcta     60
caagagtatc tcactacaag ccctctagac ccttgtttcg acctcatgaa ccgggattac    120
acttgtgagt taagagatag tcttttgtgg tctgagggat tgtttccggc tggacctttt    180
cgcgatgcac agtcctcaat ctgcgagaat ctgtcagctg atagtccagt gtcagccaat    240
aaacctgagg taagaggagg agttaggaga accacaagtg gatcttctca tgttaactct    300
gatgacgaag atgccgagac agaagcaggg caatctgaaa tgactaatga tcccaatgat    360
ctgaaacgta ttagaaggat gaactcaaac agggaatcag caaagaggtc gaggagaagg    420
aagcaagagt acttggtaga tcttgagact caggttgatt ctttgaaagg cgataactca    480
acactgtaca agcagctcat agacgcaaca caacagtttc gtagcgctgg aacaaataac    540
agagttctca aatcagatgt tgaaactctg agagtcaagg tgaaactagc agaagatttg    600
gtagcgagag ggtcactcac tagcagcttg aatcaacttc tacaaactca tctaagtcca    660
ccatcacact ccatcagcag tctgcactac acgggaaata cctcgcccgc cattacagtc    720
cacagtgacc aatctttgtt ccctggaatg acactttctg gacagaactc aagccctgga    780
cttggtaatg tatccagtga agctgttagc tgcgtctcag acatctggcc atga          834

<210> SEQ ID NO 2
<211> LENGTH: 277
<212> TYPE: PRT
<213> ORGANISM: Arabidopsis thaliana

<400> SEQUENCE: 2

Met Asp Asn His Thr Ala Lys Asp Ile Gly Met Lys Arg Ser Ala Ser
1               5                   10                  15

Glu Leu Ala Leu Gln Glu Tyr Leu Thr Thr Ser Pro Leu Asp Pro Cys
            20                  25                  30

Phe Asp Leu Met Asn Arg Asp Tyr Thr Cys Glu Leu Arg Asp Ser Leu
        35                  40                  45

Leu Trp Ser Glu Gly Leu Phe Pro Ala Gly Pro Phe Arg Asp Ala Gln
    50                  55                  60

Ser Ser Ile Cys Glu Asn Leu Ser Ala Asp Ser Pro Val Ser Ala Asn
65                  70                  75                  80

Lys Pro Glu Val Arg Gly Gly Val Arg Arg Thr Thr Ser Gly Ser Ser
                85                  90                  95

His Val Asn Ser Asp Asp Glu Asp Ala Glu Thr Glu Ala Gly Gln Ser
```

|   |   | 100 |   |   |   | 105 |   |   |   | 110 |   |   |
|---|---|---|---|---|---|---|---|---|---|---|---|---|
| Glu | Met | Thr | Asn | Asp | Pro | Asn | Asp | Leu | Lys | Arg | Ile | Arg | Arg | Met | Asn |
|   |   |   | 115 |   |   |   |   | 120 |   |   |   |   | 125 |   |   |
| Ser | Asn | Arg | Glu | Ser | Ala | Lys | Arg | Ser | Arg | Arg | Lys | Gln | Glu | Tyr |
|   |   | 130 |   |   |   |   | 135 |   |   |   |   | 140 |   |   |
| Leu | Val | Asp | Leu | Glu | Thr | Gln | Val | Asp | Ser | Leu | Lys | Gly | Asp | Asn | Ser |
| 145 |   |   |   |   | 150 |   |   |   |   | 155 |   |   |   |   | 160 |
| Thr | Leu | Tyr | Lys | Gln | Leu | Ile | Asp | Ala | Thr | Gln | Gln | Phe | Arg | Ser | Ala |
|   |   |   |   | 165 |   |   |   |   | 170 |   |   |   |   | 175 |   |
| Gly | Thr | Asn | Asn | Arg | Val | Leu | Lys | Ser | Asp | Val | Glu | Thr | Leu | Arg | Val |
|   |   |   | 180 |   |   |   |   | 185 |   |   |   |   | 190 |   |   |
| Lys | Val | Lys | Leu | Ala | Glu | Asp | Leu | Val | Ala | Arg | Gly | Ser | Leu | Thr | Ser |
|   |   | 195 |   |   |   |   | 200 |   |   |   |   | 205 |   |   |   |
| Ser | Leu | Asn | Gln | Leu | Leu | Gln | Thr | His | Leu | Ser | Pro | Pro | Ser | His | Ser |
|   |   | 210 |   |   |   |   | 215 |   |   |   |   | 220 |   |   |   |
| Ile | Ser | Ser | Leu | His | Tyr | Thr | Gly | Asn | Thr | Ser | Pro | Ala | Ile | Thr | Val |
| 225 |   |   |   |   | 230 |   |   |   |   | 235 |   |   |   |   | 240 |
| His | Ser | Asp | Gln | Ser | Leu | Phe | Pro | Gly | Met | Thr | Leu | Ser | Gly | Gln | Asn |
|   |   |   |   | 245 |   |   |   |   | 250 |   |   |   |   | 255 |   |
| Ser | Ser | Pro | Gly | Leu | Gly | Asn | Val | Ser | Ser | Glu | Ala | Val | Ser | Cys | Val |
|   |   |   | 260 |   |   |   |   | 265 |   |   |   |   | 270 |   |   |
| Ser | Asp | Ile | Trp | Pro |
|   |   |   | 275 |   |

<210> SEQ ID NO 3
<211> LENGTH: 1554
<212> TYPE: DNA
<213> ORGANISM: Arabidopsis thaliana

<400> SEQUENCE: 3

```
ctgttttgta taactactct ttgttataca tagccatttt agttactctg gtttgtttct      60
catcccattc tctctctctt tctctaatgg ttcttaatct gttttagcat tttgatcatc     120
taaaactttc aatttctctc ttgatcctca cttgaatttt tgttgtttc tctcaaatct     180
ttgatccttt cctttgtttt tcatttgacc tcttacaaaa aaatctggtg tgccattaaa     240
tctttattaa tggcacaact tcctccgaaa atcccaacca tgacgacgcc aaattggcct     300
gacttctcct cccagaaact cccttccata gccgcaacgg cggcagccgc agcaaccgct     360
ggacctcaac aacaaaaccc ttcatggatg gatgagtttc tcgacttctc agcgactcgc     420
cgtgggactc accgtcgttc tataagcgac tccattgctt ccttgaacc accttcctcc     480
ggcgtcggaa accaccactt cgataggttt gacgacgagc aattcatgtc catgttcaac     540
gacgacgtac acaacaataa ccacaatcat catcatcatc acagcatcaa cggcaatgtg     600
ggtcccacgc gttcatcctc caacacctcc acgccgtccg atcataatag ccttagcgac     660
gacgacaaca caaagaagc accaccgtcc gatcatgatc atcacatgga caataatgta     720
gccaatcaaa acaacgccgc cggtaacaat tacaacgaat cagacgaggt ccaaagccag     780
tgcaagacgg agccacaaga tggtccgtcg gcgaatcaaa actccggtgg aagctccggt     840
aatcgtattc acgaccctaa aagggtaaaa agaattttag caaataggca atcagcacag     900
agatcaaggg tgaggaaatt gcaatacata tcagagcttg aaaggagcgt tacttcattg     960
cagactgaag tgtcagtgtt atcgccaaga gttgcgtttt tggatcatca gcgattgctt    1020
ctcaacgtcg acaatagtgc tatcaagcaa cgaatcgcag ctttagcaca agataagatt    1080
```

-continued

```
ttcaaagacg ctcatcaaga agcattgaag agagaaatag agagacttcg acaagtatat    1140
catcaacaaa gcctcaagaa gatggagaat aatgtctccg atcaatctcc ggccgatatc    1200
aaaccgtccg ttgagaagga acagctcctc aatgtctaaa gctgttcgtt cactaagatc    1260
tttcttttca tggcgaaaag attcttgact ataaaacctc tttgtgtcaa gaaattaatt    1320
tatcaaagaa gatggccttt tttatttgat ctaatcacat tttttaagt tgtgatgaat     1380 ttgcttttga tgtatctgtt tttttttttt tttcttatgg agtgggaggg ggaaagtggg    1440
aatgatatgt aaaagaact tagctgattt gttgtttatt caatttttt gttggagtgt      1500 ctatgcattg tgtactaatt gatatttttt ccgaatgatt tttttttcca tcaa          1554
```

```
<210> SEQ ID NO 4
<211> LENGTH: 329
<212> TYPE: PRT
<213> ORGANISM: Arabidopsis thaliana

<400> SEQUENCE: 4
```

```
Met Ala Gln Leu Pro Pro Lys Ile Pro Thr Met Thr Thr Pro Asn Trp
1               5                  10                  15

Pro Asp Phe Ser Ser Gln Lys Leu Pro Ser Ile Ala Ala Thr Ala Ala
            20                  25                  30

Ala Ala Thr Ala Gly Pro Gln Gln Gln Asn Pro Ser Trp Met Asp
        35                  40                  45

Glu Phe Leu Asp Phe Ser Ala Thr Arg Arg Gly Thr His Arg Arg Ser
    50                  55                  60

Ile Ser Asp Ser Ile Ala Phe Leu Glu Pro Pro Ser Ser Gly Val Gly
65                  70                  75                  80

Asn His His Phe Asp Arg Phe Asp Glu Gln Phe Met Ser Met Phe
                85                  90                  95

Asn Asp Asp Val His Asn Asn Asn His Asn His His His His Ser
            100                 105                 110

Ile Asn Gly Asn Val Gly Pro Thr Arg Ser Ser Ser Asn Thr Ser Thr
        115                 120                 125

Pro Ser Asp His Asn Ser Leu Ser Asp Asp Asn Asn Lys Glu Ala
    130                 135                 140

Pro Pro Ser Asp His Asp His His Met Asp Asn Asn Val Ala Asn Gln
145                 150                 155                 160

Asn Asn Ala Ala Gly Asn Asn Tyr Asn Glu Ser Asp Glu Val Gln Ser
                165                 170                 175

Gln Cys Lys Thr Glu Pro Gln Asp Gly Pro Ser Ala Asn Gln Asn Ser
            180                 185                 190

Gly Gly Ser Ser Gly Asn Arg Ile His Asp Pro Lys Arg Val Lys Arg
        195                 200                 205

Ile Leu Ala Asn Arg Gln Ser Ala Gln Arg Ser Arg Val Arg Lys Leu
    210                 215                 220

Gln Tyr Ile Ser Glu Leu Glu Arg Ser Val Thr Ser Leu Gln Thr Glu
225                 230                 235                 240

Val Ser Val Leu Ser Pro Arg Val Ala Phe Leu Asp His Gln Arg Leu
                245                 250                 255

Leu Leu Asn Val Asp Asn Ser Ala Ile Lys Gln Arg Ile Ala Ala Leu
            260                 265                 270

Ala Gln Asp Lys Ile Phe Lys Asp Ala His Gln Glu Ala Leu Lys Arg
        275                 280                 285

Glu Ile Glu Arg Leu Arg Gln Val Tyr His Gln Gln Ser Leu Lys Lys
```

```
                    290                 295                 300
Met Glu Asn Asn Val Ser Asp Gln Ser Pro Ala Asp Ile Lys Pro Ser
305                 310                 315                 320

Val Glu Lys Glu Gln Leu Leu Asn Val
                325
```

<210> SEQ ID NO 5
<211> LENGTH: 1728
<212> TYPE: DNA
<213> ORGANISM: Hevea brasiliensis

<400> SEQUENCE: 5

| | | | | | |
|---|---|---|---|---|---|
| atggacacca | ccggccggct | ccaccaccga | aagcatgcta | cacccgttga | ggaccgttct | 60 |
| ccgaccactc | cgaaagcgtc | ggacgcgctt | ccgcttcccc | tctacctgac | caacgcggtt | 120 |
| ttcttcacgc | tgttcttctc | ggtggcgtat | acctccttc | accggtggcg | cgacaagatc | 180 |
| cgcaactcca | ctccccttca | tatcgttact | ctctctgaaa | ttgttgctat | tgtctccctc | 240 |
| attgcctctt | tcatttacct | cctaggattc | ttcggtatcg | attttgtgca | gtcattcatt | 300 |
| gcacgcgcct | cccatgacgt | gtgggacctc | gaagatacgg | atcccaacta | cctcatcgat | 360 |
| gaagatcacc | gtcgttac | ttgccctccc | gctaatatat | ctactaagac | taccattatt | 420 |
| gccgcaccta | ccaaattgcc | tacctcggaa | cccttaattg | cacccttagt | ctcggaggaa | 480 |
| gacgaaatga | tcgtcaactc | cgtcgtggat | gggaagatac | cctcctattc | tctggagtcg | 540 |
| aagctcgggg | actgcaaacg | agcggctgcg | attcgacgcg | aggctttgca | gaggatgaca | 600 |
| aggaggtcgc | tggaaggctt | gccagtagaa | gggttcgatt | acgagtcgat | tttaggacaa | 660 |
| tgctgtgaaa | tgccagtggg | atacgtgcag | attccggtgg | ggattgcggg | gccgttgttg | 720 |
| ctgaacgggc | gggagtactc | tgttccaatg | gcgaccacgg | agggttgttt | ggtggcgagc | 780 |
| actaatagag | ggtgtaaggc | gatttacttg | tcaggtgggg | ccaccagcgt | cttgttgaag | 840 |
| gatggcatga | caagagcgcc | tgttgtaaga | ttcgcgtcgg | cgactagagc | cgcggagttg | 900 |
| aagttcttct | tggaggatcc | tgacaatttt | gataccttgg | ccgtagtttt | taacaagtcc | 960 |
| agtagatttg | cgaggctcca | aggcattaaa | tgctcaattg | ctggtaagaa | tctttatata | 1020 |
| agattcagct | gcagcactgg | cgatgcaatg | gggatgaaca | tggtttctaa | aggggttcaa | 1080 |
| aacgttcttg | aatttcttca | aagtgatttt | tctgatatgg | atgtcattgg | aatctcagga | 1140 |
| aattttgtt | cggataagaa | gcctgctgct | gtaaattgga | ttgaaggacg | tggcaaatca | 1200 |
| gttgtttgtg | aggcaattat | caaggaagag | gtggtgaaga | aggtgttgaa | accaatgtg | 1260 |
| gcctccctag | tggagcttaa | catgctcaag | aatcttgctg | ttctgctgt | tgctggtgct | 1320 |
| ttgggtggat | ttaatgccca | tgcaggcaac | atcgtatctg | caatctttat | tgccactggc | 1380 |
| caggatccag | cacagaatgt | tgagagttct | cattgcatta | ccatgatgga | agctgtcaat | 1440 |
| gatgaaaagg | atctccatat | ctctgtgacc | atgccctcca | ttgaggtggg | tacagtcgga | 1500 |
| ggtggaactc | aacttgcatc | tcagtctgct | tgtctcaatt | tgcttggggt | gaagggtgca | 1560 |
| aacaaagagt | cgccaggatc | aaactcaagg | ctccttgctg | ccatcgtagc | tggttcagtt | 1620 |
| ttggctggtg | agctctcctt | gatgtctgcc | attgcagctg | ggcagcttgt | caagagtcac | 1680 |
| atgaagtaca | acagctccag | caaagatatg | tctaaagctg | catcttag | | 1728 |

<210> SEQ ID NO 6
<211> LENGTH: 575
<212> TYPE: PRT
<213> ORGANISM: Hevea brasiliensis

<400> SEQUENCE: 6

```
Met Asp Thr Thr Gly Arg Leu His His Arg Lys His Ala Thr Pro Val
1               5                   10                  15

Glu Asp Arg Ser Pro Thr Thr Pro Lys Ala Ser Asp Ala Leu Pro Leu
            20                  25                  30

Pro Leu Tyr Leu Thr Asn Ala Val Phe Phe Thr Leu Phe Phe Ser Val
        35                  40                  45

Ala Tyr Tyr Leu Leu His Arg Trp Arg Asp Lys Ile Arg Asn Ser Thr
    50                  55                  60

Pro Leu His Ile Val Thr Leu Ser Glu Ile Val Ala Ile Val Ser Leu
65                  70                  75                  80

Ile Ala Ser Phe Ile Tyr Leu Leu Gly Phe Gly Ile Asp Phe Val
                85                  90                  95

Gln Ser Phe Ile Ala Arg Ala Ser His Asp Val Trp Asp Leu Glu Asp
                100                 105                 110

Thr Asp Pro Asn Tyr Leu Ile Asp Glu Asp His Arg Leu Val Thr Cys
            115                 120                 125

Pro Pro Ala Asn Ile Ser Thr Lys Thr Thr Ile Ile Ala Ala Pro Thr
130                 135                 140

Lys Leu Pro Thr Ser Glu Pro Leu Ile Ala Pro Leu Val Ser Glu Glu
145                 150                 155                 160

Asp Glu Met Ile Val Asn Ser Val Val Asp Gly Lys Ile Pro Ser Tyr
                165                 170                 175

Ser Leu Glu Ser Lys Leu Gly Asp Cys Lys Arg Ala Ala Ala Ile Arg
            180                 185                 190

Arg Glu Ala Leu Gln Arg Met Thr Arg Arg Ser Leu Glu Gly Leu Pro
        195                 200                 205

Val Glu Gly Phe Asp Tyr Glu Ser Ile Leu Gly Gln Cys Cys Glu Met
210                 215                 220

Pro Val Gly Tyr Val Gln Ile Pro Val Gly Ile Ala Gly Pro Leu Leu
225                 230                 235                 240

Leu Asn Gly Arg Glu Tyr Ser Val Pro Met Ala Thr Thr Glu Gly Cys
                245                 250                 255

Leu Val Ala Ser Thr Asn Arg Gly Cys Lys Ala Ile Tyr Leu Ser Gly
            260                 265                 270

Gly Ala Thr Ser Val Leu Leu Lys Asp Gly Met Thr Arg Ala Pro Val
        275                 280                 285

Val Arg Phe Ala Ser Ala Thr Arg Ala Ala Glu Leu Lys Phe Phe Leu
    290                 295                 300

Glu Asp Pro Asp Asn Phe Asp Thr Leu Ala Val Val Phe Asn Lys Ser
305                 310                 315                 320

Ser Arg Phe Ala Arg Leu Gln Gly Ile Lys Cys Ser Ile Ala Gly Lys
                325                 330                 335

Asn Leu Tyr Ile Arg Phe Ser Tyr Ser Thr Gly Asp Ala Met Gly Met
            340                 345                 350

Asn Met Val Ser Lys Gly Val Gln Asn Val Leu Glu Phe Leu Gln Ser
        355                 360                 365

Asp Phe Ser Asp Met Asp Val Ile Gly Ile Ser Gly Asn Phe Cys Ser
    370                 375                 380

Asp Lys Lys Pro Ala Ala Val Asn Trp Ile Glu Gly Arg Gly Lys Ser
385                 390                 395                 400

Val Val Cys Glu Ala Ile Ile Lys Glu Glu Val Val Lys Lys Val Leu
```

|     |     |     |     |     | 405 |     |     |     |     | 410 |     |     |     |     | 415 |
| --- | --- | --- | --- | --- | --- | --- | --- | --- | --- | --- | --- | --- | --- | --- | --- |

Lys Thr Asn Val Ala Ser Leu Val Glu Leu Asn Met Leu Lys Asn Leu
            420                 425                 430

Ala Gly Ser Ala Val Ala Gly Ala Leu Gly Gly Phe Asn Ala His Ala
            435                 440                 445

Gly Asn Ile Val Ser Ala Ile Phe Ile Ala Thr Gly Gln Asp Pro Ala
            450                 455                 460

Gln Asn Val Glu Ser Ser His Cys Ile Thr Met Met Glu Ala Val Asn
465                 470                 475                 480

Asp Gly Lys Asp Leu His Ile Ser Val Thr Met Pro Ser Ile Glu Val
                485                 490                 495

Gly Thr Val Gly Gly Gly Thr Gln Leu Ala Ser Gln Ser Ala Cys Leu
            500                 505                 510

Asn Leu Leu Gly Val Lys Gly Ala Asn Lys Glu Ser Pro Gly Ser Asn
            515                 520                 525

Ser Arg Leu Leu Ala Ala Ile Val Ala Gly Ser Val Leu Ala Gly Glu
            530                 535                 540

Leu Ser Leu Met Ser Ala Ile Ala Ala Gly Gln Leu Val Lys Ser His
545                 550                 555                 560

Met Lys Tyr Asn Arg Ser Ser Lys Asp Met Ser Lys Ala Ala Ser
                565                 570                 575

<210> SEQ ID NO 7
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t

<400> SEQUENCE: 7
ntcgastwts gwgtt                                                         15

<210> SEQ ID NO 8
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t

<400> SEQUENCE: 8
ngtcgtswga nawgaa                                                        16

<210> SEQ ID NO 9
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t

```
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
<223> OTHER INFORMATION: n is a, c, g, or t

<400> SEQUENCE: 9
wgtgnagwan canag                                                    15

<210> SEQ ID NO 10
<211> LENGTH: 15
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (9)..(9)
<223> OTHER INFORMATION: n is a, c, g, or t
<220> FEATURE:
<221> NAME/KEY: misc_feature
<222> LOCATION: (12)..(12)
<223> OTHER INFORMATION: n is a, c, g, or t

<400> SEQUENCE: 10
sttntastnc tntgc                                                    15

<210> SEQ ID NO 11
<211> LENGTH: 17
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (9)..(9)
<223> OTHER INFORMATION: n is a, c, g, or t

<400> SEQUENCE: 11
sstggstana twatwct                                                  17

<210> SEQ ID NO 12
<211> LENGTH: 16
<212> TYPE: DNA
<213> ORGANISM: Artificial Sequence
<220> FEATURE:
<223> OTHER INFORMATION: Synthetic primer
<220> FEATURE:
<221> NAME/KEY: misc_feature
<222> LOCATION: (5)..(5)
<223> OTHER INFORMATION: n is a, c, g, or t
<220> FEATURE:
<221> NAME/KEY: misc_feature
<222> LOCATION: (10)..(10)
<223> OTHER INFORMATION: n is a, c, g, or t
<220> FEATURE:
<221> NAME/KEY: misc_feature
<222> LOCATION: (13)..(13)
```

<223> OTHER INFORMATION: n is a, c, g, or t

<400> SEQUENCE: 12
agwgnagwan canaga                                               16

<210> SEQ ID NO 13
<211> LENGTH: 1565
<212> TYPE: DNA
<213> ORGANISM: Hevea brasiliensis

<400> SEQUENCE: 13

```
ctctgcttcg cacgagtagc gttctaaatc taccaaggat gattacgaaa ggggaagcaa      60
tccttccagg aatcaaaaaa agggacatgc caatgaatgc tcgttttatt accctacaag    120
tacagtgcaa ggttgggtca gtgaatagag ttattggcac agccatgttt cctgtttcta    180
attcttggga ggttatacac aagtgaattt tgagttacag gctgagggat gaaaagaatg    240
gaattgttac actgtatttg gtagggagaa aagtaagaga ggaagaaaaa tataagaaa     300
aaataagttt attttttatt gttttgttta aattgaataa aaataaaga agcgtaaaaa     360
tattaaaagg aaaataaaaa tattttatct ttttttcctt ttctctttaa aatagagaaa   420
aatgagagga aaatatttaa aagtataaat ataactctat atttaataat tttttttaaa   480
atttaaaaat aaaattataa tttattatt cataaaataa ttttttctca aatattttc     540
tctttcaatc cagataaaaa gaaaaaaaat aatttttatt ttcattcttt attttctctc   600
ttttaatttt ctttctccct gaaatattcc caaacacagt gttaatgttt ttgtaaaaag   660
gggcaagcag tagcagatca cgtgagaaag aatttgccta tagtattgcc cgtgttcttc   720
ctcgtcatcg ttgttgcggc caacctaatt tatcatggag gagtagtgcc agggatttca   780
cgtttggcgt acttctggtg cttaattaat ttatttgggg ttttgtattt taaaattagg   840
taaaatttct ataattttac aaaaattaac ttattttatt aaaaattaaa agatttagac   900
taaatagcaa aatcacgcaa tgggtttagt gttttaatac gagattagac ataataataa   960
taacacctga tggtcctcta ttttcaatta tttgccaact aaaccacaat caaccatgtt  1020
caacacaatt ggaattctac tgatatatca ttacagctgc caaaacattt atttaggcca  1080
ttaatcaatt ttaattgaac atgctatttt tctatcatca attcagcttc tttttttata  1140
ttaatttaat ttataattaa cactaatgac aaaattagat attaaattta tgagaatgaa  1200
acataaaatt aatatataaa aaatatatta gttttaaaaa taattttaaa tattaaactc  1260
aaaatattat atatatatat atatatatat atatatgaaa ttaaaatttt aaattaaaaa  1320
aatgcagtaa aaaaaaaaaa aataataaag tagctattgg atccaagggt ggtttagaac  1380
gctactcgtg cgaagcaaga gtgaggaaaa tgccaaggac ccgtcacgca cgccacatgt  1440
gtggggagga ggctcccgtt ctcgcattct tataaaaatg tcccagatcc aaatctcctg  1500
aaactaagct catcattccc tcttcctcct ctcccttttct ctctcctgcg ccggcatatt  1560
tttac                                                              1565
```

METHOD FOR ADJUSTING EXPRESSION OF HYDROXYMETHYLGLUTARYL COA REDUCTASE USING BZIP-TYPE TRANSCRIPTION FACTOR, ISOPRENOID-PRODUCING PLANT INTO WHICH GENE ENCODED FOR BZIP-TYPE TRANSCRIPTION FACTOR IS INTRODUCED, AND METHOD FOR MANUFACTURING POLYISOPRENOID IN WHICH SAID PLANT IS USED

REFERENCE TO SEQUENCE LISTING SUBMITTED VIA EFS-WEB

This application is includes an electronically submitted sequence listing in .txt format. The .txt file contains a sequence listing entitled "2016-04-14_5051-0387PUS1_ST25.txt" created on Apr. 14, 2016 and is 20,844 bytes in size. The sequence listing contained in this .txt file is part of the specification and is hereby incorporated by reference herein in its entirety.

TECHNICAL FIELD

The present invention relates to a method of regulating the expression of hydroxymethylglutaryl-CoA reductase by a bZIP transcription factor, an isoprenoid-producing plant into which has been introduced a gene encoding a bZIP transcription factor, and a method of producing a polyisoprenoid using the isoprenoid-producing plant.

BACKGROUND ART

Nowadays natural rubber (one example of polyisoprenoids) for use in industrial rubber products can be harvested from rubber-producing plants, such as *Hevea brasiliensis* (Para rubber tree) belonging to the family Euphorbiaceae, or *Ficus elastica* (Indian rubber tree) belonging to the family Moraceae.

At present, *Hevea brasiliensis* is practically the only one source of natural rubber for industrial rubber products. *Hevea brasiliensis* is a plant that can grow only in limited areas such as in Southeast Asia and South America. Moreover, *Hevea brasiliensis* requires about seven years from planting to mature enough for rubber extraction, and the period during which natural rubber can be extracted is limited to 20 to 30 years. Although more natural rubber is expected to be needed mainly by developing countries in years to come, for the reason mentioned above it is difficult to greatly increase the production of natural rubber using *Hevea brasiliensis*. Depletion of natural rubber sources is therefore of concern and there are needs for stable natural rubber sources other than mature *Hevea brasiliensis* and for improvement in productivity of natural rubber from *Hevea brasiliensis*.

For example, an approach to improve productivity of natural rubber from *Hevea brasiliensis* is to extract more latex to produce more natural rubber. Specifically, such methods include a method of stimulating the trunk of rubber trees with ethylene or ethephon (2-chloroethylphosphonic acid); and a method of accelerating laticifer differentiation using lanolin containing jasmonic acid, linolenic acid, which is a precursor of jasmonic acid, or the like (see, for example, Non Patent Literature 1).

Unfortunately, if the method of increasing latex production via ethylene stimulation is applied to the trunk for a long term, then cracks may easily be generated in the bark. In addition, the aim of the ethylene stimulation is to allow latex to exude more smoothly from laticifers and is not to directly improve the tree's ability to produce latex, and this method provides only a limited and insufficient increase in latex production.

Although jasmonic acid or the like can be used to accelerate laticifer formation and thereby increase the number of laticifers, this method also has the problem that latex exuding from laticifers can coagulate at the cuts during the collection of latex by tapping, and therefore the produced latex may not be sufficiently collected.

It is also known that some factors, including light responses, wound responses, and cold treatment, affect polyisoprenoid biosynthesis. However, it is not specifically known which transcription factor is activated in such a response to regulate polyisoprenoid biosynthesis.

CITATION LIST

Non Patent Literature

Non Patent Literature 1: Hao et al., Annals of Botany, 2000, Vol. 85, pp. 37-43

SUMMARY OF INVENTION

Technical Problem

The present invention was made to overcome the above problems, and an object of the present invention is to provide a method for enhancing the pathway of polyisoprenoid biosynthesis. Further objects of the present invention are to provide an isoprenoid-producing plant having an enhanced pathway of polyisoprenoid biosynthesis, and to provide a method of producing a polyisoprenoid using the isoprenoid-producing plant.

Solution to Problem

The present invention relates to a method of regulating the expression of hydroxymethylglutaryl-CoA reductase by a bZIP transcription factor.

Preferably, the method includes introducing a gene encoding the bZIP transcription factor into a host to regulate the expression of hydroxymethylglutaryl-CoA reductase in the host.

The gene is preferably either of the following DNAs:

[1] a DNA having the base sequence of SEQ ID NO: 1 or 3; and

[2] a DNA encoding a protein with transcription factor activity and capable of hybridizing under stringent conditions to a DNA having a base sequence complementary to the base sequence of SEQ ID NO: 1 or 3.

The method is more preferably used to enhance the expression of hydroxymethylglutaryl-CoA reductase.

The bZIP transcription factor is preferably any of the following proteins:

[1] a protein having the amino acid sequence of SEQ ID NO: 2 or 4;

[2] a protein having transcription factor activity and having an amino acid sequence containing one or more amino acid substitutions, deletions, insertions and/or additions relative to the amino acid sequence of SEQ ID NO: 2 or 4; and

[3] a protein having transcription factor activity and having an amino acid sequence that has at least 80% sequence identity to the amino acid sequence of SEQ ID NO: 2 or 4.

The host is preferably an isoprenoid-producing plant.

The present invention also relates to an isoprenoid-producing plant, into which has been introduced a gene encoding a bZIP transcription factor.

The gene is preferably either of the following DNAs:

[1] a DNA having the base sequence of SEQ ID NO: 1 or 3; and

[2] a DNA encoding a protein with transcription factor activity and capable of hybridizing under stringent conditions to a DNA having a base sequence complementary to the base sequence of SEQ ID NO: 1 or 3.

The present invention further relates to a method of producing a polyisoprenoid using the isoprenoid-producing plant.

Advantageous Effects of Invention

Since the method of the present invention is a method of regulating by a bZIP transcription factor the expression of hydroxymethylglutaryl-CoA reductase that is a rate-limiting factor in the mevalonic acid (MVA) pathway, which is upstream in the polyisoprenoid biosynthesis pathway, the method enhances the rate-limiting step of isopentenyl diphosphate (IPP) biosynthesis in the MVA pathway, so that the polyisoprenoid biosynthesis pathway can be suitably enhanced. Moreover, the isoprenoid-producing plant of the present invention, into which has been introduced a gene encoding a bZIP transcription factor, has a suitably enhanced pathway of polyisoprenoid biosynthesis, and can be used in the production of polyisoprenoids to increase polyisoprenoid production.

DESCRIPTION OF EMBODIMENTS

Figure 1:
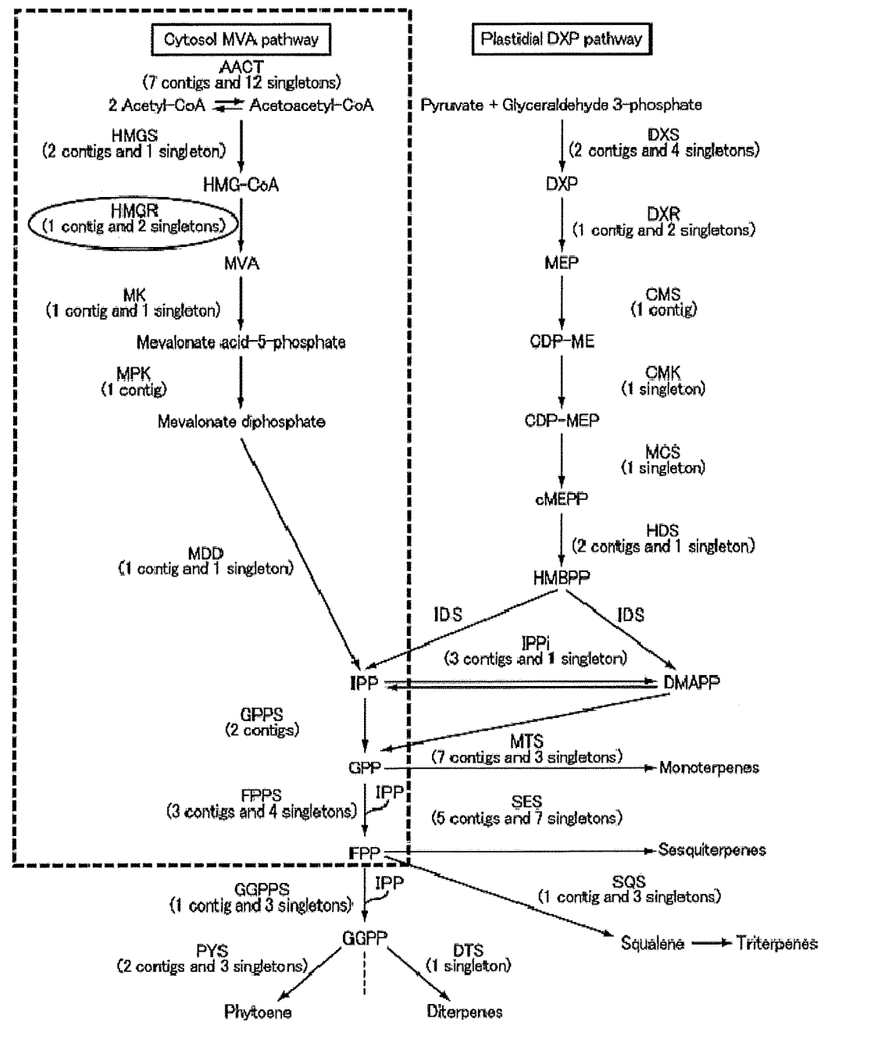
FIG. 1 is a schematic view of a part of the polyisoprenoid biosynthesis pathway.

The present inventors have studied various ways to enhance the polyisoprenoid biosynthesis pathway. FIG. 1 shows a part of the polyisoprenoid biosynthesis pathway. There are two known pathways for biosynthesis of isopentenyl diphosphate (IPP), which is an important member of the polyisoprenoid biosynthesis pathway: mevalonic acid (MVA) pathway (cytosol MVA pathway shown in FIG. 1); and MEP pathway (plastidial DXP pathway shown in FIG. 1).

The present inventors focused on the MVA pathway which is a common pathway that supplies IPP in rubber latex synthesis, and selected, from various proteins involved in the polyisoprenoid biosynthesis pathway, some proteins that are expected to have'important roles in view of enhancing the pathway enclosed in the dotted line in FIG. 1. Further, they found out that, among these proteins, hydroxymethyl-glutaryl-CoA reductase (HMG-CoA reductase) is a rate-limiting factor in the MVA pathway.

In order to regulate the expression of HMG-CoA reductase, the present inventors then sought a transcription factor capable of regulating the expression of HMG-CoA reductase. Specifically, a DNA fragment from leaves of *Hevea brasiliensis* which contains a gene encoding HMG-CoA reductase (the amino acid sequence of HMG-CoA reductase is set forth in the sequence listing as SEQ ID NO: 6) (the base sequence of the gene is set forth in the sequence listing as SEQ ID NO: 5) and its promoter region was cloned (see EXAMPLES for details). The base sequence of the resulting DNA fragment was analyzed to reveal the base sequence of the promoter region of the gene encoding HMG-CoA reductase.

Additionally, the revealed base sequence of the promoter region was analyzed using a plant promoter database (a database of plant cis-acting regulatory DNA elements (PLACE)). A bZIP transcription factor binding (recognition) site (ACACNNG) was found as a result of the analysis.

These results strongly suggest that bZIP transcription factors are transcription factors capable of regulating the expression of HMG-CoA reductase, or in other words, transcription factors that enhance the rate-limiting step of IPP biosynthesis in the MVA pathway and can suitably regulate the polyisoprenoid biosynthesis pathway. Then, a validation test using yeast cells was performed to confirm that the expression of HMG-CoA reductase is enhanced by the use of BZIP9 (the base sequence and the amino acid sequence of BZIP9 from *Arabidopsis thaliana* are set forth in the sequence listing as SEQ ID NOs: 1 and 2, respectively), or BZIP61 (the base sequence and the amino acid sequence of BZIP61 from *Arabidopsis thaliana* are set forth in the sequence listing as SEQ ID NOs: 3 and 4, respectively) among bZIP transcription factors.

As described above, the present inventors have found that bZIP transcription factors can suitably enhance the expression of HMG-CoA reductase, and thus enhance the rate-limiting step of IPP biosynthesis in the MVA pathway and can thereby suitably enhance the polyisoprenoid biosynthesis pathway. Another finding is that since the bZIP transcription factors enhance the rate-limiting step of IPP biosynthesis in the MVA pathway and can thereby suitably enhance the polyisoprenoid biosynthesis pathway, an isoprenoid-producing plant into which has been introduced a gene encoding such an bZIP transcription factor can be used in the production of polyisoprenoids to increase polyisoprenoid production.

As used herein, "hydroxymethylglutaryl-CoA reductase (HMG-CoA reductase)" is a rate-limiting enzyme of the mevalonic acid pathway and is intended to include both hydroxymethylglutaryl-CoA reductase (NADPH) (EC 1.1.1.34) and hydroxymethylglutaryl-CoA reductase (EC 1.1.1.88).

The method of the present invention is a method of regulating the expression of hydroxymethylglutaryl-CoA reductase by a bZIP transcription factor.

The bZIP transcription factor is not particularly limited, as long as it is a transcription factor structurally featuring a leucine zipper motif with a basic region. Examples include BZIP9 (the base sequence and the amino acid sequence of BZIP9 from *Arabidopsis thaliana* are set forth in the sequence listing as SEQ ID NOs: 1 and 2, respectively), and BZIP61 (the base sequence and the amino acid sequence of BZIP61 from *Arabidopsis thaliana* are set forth in the sequence listing as SEQ ID NOs: 3 and 4, respectively).

The term "transcription factor" as used herein refers to a protein having an activity of increasing or decreasing (preferably increasing) the rate of transcription of a gene or genes.

The origin of the bZIP transcription factor is not particularly limited, but the bZIP transcription factor is preferably a transcription factor from *Hevea brasiliensis, Sonchus oleraceus, Parthenium argentatum, Taraxacum koksaghyz*, or *Arabidopsis thaliana*.

(Amino Acid Sequence of bZIP Transcription Factor)

The following protein [1] is a specific example of the bZIP transcription factor:

[1] a protein having the amino acid sequence of SEQ ID NO: 2 or 4;

Moreover, it is known that some transcription factors have transcription factor activity even when one or more amino acid substitutions, deletions, insertions, or additions are introduced into their original amino acid sequences. Considering this fact, another specific example of the bZIP transcription factor is the following protein [2]:

[2] a protein having transcription factor activity and having an amino acid sequence containing one or more amino acid substitutions, deletions, insertions and/or additions relative to the amino acid sequence of SEQ ID NO: 2 or 4.

The term "transcription factor activity" as used herein refers to an activity of increasing or decreasing (preferably increasing) the rate of transcription of a gene encoding hydroxymethylglutaryl-CoA reductase.

In order to maintain transcription factor activity, the number of amino acid substitutions, deletions, insertions, and/or additions relative to the amino acid sequence of SEQ ID NO: 2 is preferably 1 or more, more preferably 1 to 55, still more preferably 1 to 41, particularly preferably 1 to 27, most preferably 1 to 13, even most preferably 1 to 5, and still even most preferably 1 or 2.

Also in order to maintain transcription factor activity, the number of amino acid substitutions, deletions, insertions, and/or additions relative to the amino acid sequence of SEQ ID NO: 4 is preferably 1 or more, more preferably 1 to 65, still more preferably 1 to 49, particularly preferably 1 to 32, most preferably 1 to 16, even most preferably 1 to 6, and still even most preferably 1 to 3.

Among other amino acid substitutions, conservative substitutions are preferred. Specific examples include substitutions within each of the following groups in the parentheses: (glycine, alanine), (valine, isoleucine, leucine), (aspartic acid, glutamic acid), (asparagine, glutamine), (serine, threonine), (lysine, arginine) and (phenylalanine, tyrosine).

The amino acid substitutions, deletions, insertions, and/or additions are preferably introduced into regions other than the bZIP transcription factor activity domains, binding domains that bind to transcription factor binding sites, and other important portions involved in transcription factor activity. Those skilled in the art can appropriately identify such domains by homology analysis with a known bZIP transcription factor.

It is also known that some proteins with amino acid sequences having high sequence identity to the amino acid sequence of a transcription factor also have similar activity. Considering this fact, another specific example of the bZIP transcription factor is the following protein [3]:

[3] a protein having transcription factor activity and having an amino acid sequence that has at least 80% sequence identity to the amino acid sequence of SEQ ID NO: 2 or 4.

For maintenance of transcription factor activity, the sequence identity to the amino acid sequence of SEQ ID NO: 2 or 4 is preferably at least 85%, more preferably at least 90%, still more preferably at least 95%, particularly preferably at least 98%, most preferably at least 99%.

The sequence identity between amino acid sequences or base sequences may be determined using the algorithm BLAST [Pro. Natl. Acad. Sci. USA, 90, 5873 (1993)] developed by Karlin and Altschul or FASTA [Methods Enzymol., 183, 63 (1990)].

Whether a protein has transcription factor activity may be determined by conventionally known techniques, such as gel shift assays, or reporter assays using a reporter gene encoding β-galactosidase, luciferase, green fluorescent protein (GFP), or the like.

The bZIP transcription factor is preferably any of the following proteins:

[1-1] a protein having the amino acid sequence of SEQ ID NO: 2;

[2-1] a protein having transcription factor activity and having an amino acid sequence containing one or more amino acid substitutions, deletions, insertions, and/or additions relative to the amino acid sequence of SEQ ID NO: 2; and

[3-1] a protein having transcription factor activity and having an amino acid sequence that has at least 80% sequence identity to the amino acid sequence of SEQ ID NO: 2.

(DNA Encoding bZIP Transcription Factor)

Moreover, the DNA encoding the bZIP transcription factor may be either of the following DNAs:

[1] a DNA having the base sequence of SEQ ID NO: 1 or 3; and

[2] a DNA encoding a protein with transcription factor activity and capable of hybridizing under stringent conditions to a DNA having a base sequence complementary to the base sequence of SEQ ID NO: 1 or 3.

As used herein, the term "hybridizing" means a process in which a DNA hybridizes to a DNA having a specific base sequence or a part of the DNA. Accordingly, the DNA having a specific base sequence or part of the DNA may have a base sequence long enough to be usable as a probe in Northern or Southern blot analysis or as an oligonucleotide primer in polymerase chain reaction (PCR) analysis. The DNA used as a probe may have a length of at least 100 bases, preferably at least 200 bases, and more preferably at least 500 bases although it may be a DNA of at least 10 bases, and preferably of at least 15 bases in length.

Techniques to perform DNA hybridization experiments are well known. The hybridization conditions under which experiments are performed may be determined according to, for example, Molecular Cloning, 2nd ed. and 3rd ed. (2001), Methods for General and Molecular Bacteriology, ASM Press (1994), Immunology methods manual, Academic press (Molecular), and many other standard textbooks.

The stringent conditions may include, for example, an overnight incubation at 42° C. of a DNA-immobilized filter and a DNA probe in a solution containing 50% formamide, 5×SSC (750 mM sodium chloride and 75 mM sodium citrate), 50 mM sodium phosphate (pH 7.6), 5×Denhardt's solution, 10% dextran sulfate, and 20 μg/l denatured salmon sperm DNA, followed by washing the filter for example in a 0.2×SSC solution at approximately 65° C. Less stringent conditions may also be used. Changes in the stringency may be accomplished through the manipulation of formamide concentration (lower percentages of formamide result in lower stringency), salt concentrations or temperature. For example, low stringent conditions include an overnight incubation at 37° C. in a solution containing 6×SSCE (20×SSCE: 3 mol/l sodium chloride, 0.2 mol/l sodium dihydrogen phosphate, 0.02 mol/l EDTA, pH 7.4), 0.5% SDS, 30% formamide, and 100 μg/l denatured salmon sperm DNA, followed by washing in a 1×SSC solution containing 0.1% SDS at 50° C. In addition, to achieve even lower stringency, washes performed following hybridization may be done at higher salt concentrations (e.g. 5×SSC) in the above-mentioned low stringent conditions.

Variations in the above various conditions may be accomplished through the inclusion or substitution of blocking reagents used to suppress background in hybridization experiments. The inclusion of blocking reagents may require modification of the hybridization conditions for compatibility.

The DNA capable of hybridization under stringent conditions as described above may be a DNA having a base sequence that has at least 80%, preferably at least 90%, more preferably at least 95%, even more preferably at least 98%, and particularly preferably at least 99% sequence identity to the base sequence of SEQ ID NO: 1 or 3 as calculated using a program such as BLAST or FASTA with the parameters mentioned above.

Whether the DNA capable of hybridizing under stringent conditions to the DNA mentioned above encodes a protein having transcription factor activity may be determined by conventionally known techniques, such as gel shift assays, or reporter assays using a reporter gene encoding β-galactosidase, luciferase, green fluorescent protein (GFP), or the like.

The DNA encoding the bZIP transcription factor is preferably either of the following DNAs:

[1-1] a DNA having the base sequence of SEQ ID NO: 1; and

[2-1] a DNA encoding a protein with transcription factor activity and capable of hybridizing under stringent conditions to a DNA having a base sequence complementary to the base sequence of SEQ ID NO: 1.

The bZIP transcription factor and the DNA encoding the bZIP transcription factor may be obtained by site-directed mutagenesis of, for example, the base sequence of SEQ ID NO: 1 or 3 (the base sequence of BZIP9 from *Arabidopsis thaliana* or the base sequence of BZIP61 from *Arabidopsis thaliana*) according to site-directed mutagenesis techniques described in Molecular Cloning, A Laboratory Manual, Second Edition, Cold Spring Harbor Laboratory Press (1989), Current Protocols in Molecular Biology, John Wiley & Sons (1987-1997), Nucleic Acids Research, 10, 6487 (1982), Proc. Natl. Acad. Sci. USA, 79, 6409 (1982), Gene, 34, 315 (1985), Nucleic Acids Research, 13, 4431 (1985), Proc. Natl. Acad. Sci. USA, 82, 488 (1985), etc.

(Transformant)

The gene encoding the bZIP transcription factor can be introduced into a host to create an organism (transformant) that is transformed to express the bZIP transcription factor. Then this transformant expresses the bZIP transcription factor, which regulates (enhances) the expression of hydroxymethylglutaryl-CoA reductase. Consequently, the rate-limiting step of IPP biosynthesis in the MVA pathway is enhanced, whereby the polyisoprenoid biosynthesis pathway can be suitably enhanced and polyisoprenoid production in the transformant can be suitably increased.

The following briefly describes how to prepare an organism (transformant) that is transformed to express a bZIP transcription factor. The brief description below mainly focuses on how to prepare a transformant that is transformed to express the above-mentioned bZIP transcription factor. Once a bZIP transcription factor-encoding gene to be introduced has been determined, such a transformant can be prepared by conventionally known methods.

Specifically, for example, a DNA containing the base sequence of SEQ ID NO: 1 or 3 (the base sequence of BZIP9 from *Arabidopsis thaliana*, or the base sequence of BZIP61 from *Arabidopsis thaliana*) is inserted downstream of a promoter of an appropriate expression vector using appropriate restriction enzymes and the like to prepare a recombinant DNA, which is then introduced into host cells compatible with the expression vector to obtain a transformant.

Although the above description relates to the cases where a DNA containing the base sequence of SEQ ID NO: 1 or 3 (the base sequence of BZIP9 from *Arabidopsis thaliana*, or the base sequence of BZIP61 from *Arabidopsis thaliana*) is used, a DNA encoding any of other bZIP transcription factors from *Arabidopsis thaliana* or bZIP transcription factors from organisms other than *Arabidopsis thaliana* may be used. In such cases, screening may be performed by a known method using, for example, a part of the base sequence of SEQ ID NO: 1 as a probe to identify and isolate a DNA encoding a particular bZIP transcription factor. The method of isolating a DNA molecule of interest using a DNA molecule as a probe is described in, for example, Molecular Cloning, 2nd edition, Cold Spring Harbor Press (1989). DNAs obtained by mutagenesis of the DNAs mentioned above may also be used.

Any of microorganisms, yeasts, animal cells, insect cells, plant cells, and the like can be used as the host (host cells), as long as they are capable of expressing a gene of interest. Since the only organisms currently known to biosynthesize polyisoprenoids are plants (isoprenoid-producing plants), the host is preferably a plant (an isoprenoid-producing plant), and the host cells are preferably plant cells (cells of an isoprenoid-producing plant). Please note that if a future advance in technology allows cells other than plant cells to biosynthesize polyisoprenoids, the gene encoding the bZIP transcription factor can be suitably introduced into such cells.

The isoprenoid-producing plant is not particularly limited, provided that it is capable of producing an isoprenoid. Examples include plants of the genus *Hevea*, such as *Hevea brasiliensis*; plants of the genus *Sonchus*, such as *Sonchus oleraceus*, *Sonchus asper*, and *Sonchus brachyotus*; plants of the genus *Solidago*, such as *Solidago altissima*, *Solidago virgaurea* subsp. *asiatica*, *Solidago virgaurea* subsp. *leipcarpa*, *Solidago virgaurea* subsp. *leipc arpaf. paludosa*, *Solidago virgaurea* subsp. *gigantea*, and *Solidago gigantea* Ait. var. *leiophylla Fernald*; plants of the genus *Helianthus*, such as *Helianthus annuus*, *Helianthus argophyllus*, *Helianthus atrorubens*, *Helianthus debilis*, *Helianthus decapetalus*, and *Helianthus giganteus*; plants of the genus *Taraxacum*, such as *Taraxacum*, *Taraxacum venustum* H. Koidz, *Taraxacum hondoense* Nakai, *Taraxacum platycarpum* Dahlst, *Taraxacum japonicum*, *Taraxacum officinale* Weber, and *Taraxacum koksaghyz*; plants of the genus *Ficus*, such as *Ficus carica*, *Ficus elastica*, *Ficus pumila* L., *Ficus erecta* Thumb., *Ficus ampelas* Burm. f., *Ficus benguetensis* Merr., *Ficus irisana* Elm., *Ficus macrocarpa* L. f., *Ficus septica* Burm. f., and *Ficus benghalensis*; plants of the genus *Parthenium*, such as *Parthenium* argentatum, *Parthenium hysterophorus*, and *Parthenium hysterophorus*; and *Lactuca serriola* and *Ficus benghalensis*. In particular, the isoprenoid-producing plant is preferably at least one selected from the group consisting of plants of the genera *Hevea*, *Sonchus*, *Taraxacum* and *Parhenium*, and more preferably at least one selected from the group consisting of *Hevea brasiliensis*, *Sonchus oleraceus*, *Parthenium argentatum*, and *Taraxacum koksaghyz*.

Examples of expression vectors that can be used include vectors that are capable of autonomous replication in the host cells or of being incorporated into a chromosome thereof and contain a promoter at a position that permits transcription of the recombinant DNA.

In the case where plant cells are used as host cells, a pBI vector, a pUC vector, a Ti plasmid or tobacco mosaic virus vector, for example, may be used as an expression vector.

Any promoter that functions in plant cells can be used. Any promoter that functions in plant cells can be used. Examples include cauliflower mosaic virus (CaMV) 35S promoter and rice actin-1 promoter, nopaline synthase gene promoter, tobacco mosaic virus 35S promoter, and rice actin gene promoter.

Preferred are expression vectors with promoters that are specifically expressed in tissues in which isoprenoid compounds are biosynthesized, such as laticifers. If the promoter is specifically expressed in tissues in which polyisoprenoids are biosynthesized, retardation of plant growth and other adverse effects can be prevented.

The recombinant vector can be introduced by any method that allows the DNA to be introduced into plant cells. Examples include methods using *Agrobacterium* (JP S59-140885 A, JP S60-70080 A, WO94/00977), electroporation (JP S60-251887 A), and methods using a particle gun (gene gun) (JP 2606856 B, JP 2517813 B).

Transformants (transgenic plant cells) into which has been introduced a gene encoding a bZIP transcription factor can be prepared by these methods or the like.

The present invention provides an isoprenoid-producing plant into which has been introduced a gene encoding a bZIP transcription factor. The isoprenoid-producing plant is not particularly limited, as long as it is an isoprenoid-producing plant containing transgenic plant cells. It is intended to include, in addition to transgenic plant cells prepared by the above-described methods, for example, all their progeny or clones and even progeny plants obtained by passaging these cells. Once transgenic plant cells into which the DNA or vector has been introduced in the genome are obtained, progeny or clones can be obtained from the transgenic plant cells by sexual or asexual reproduction, tissue culture, cell culture, cell fusion, or the like. Further, the transgenic plant cells, or progeny or clones may be used to obtain reproductive materials (e.g. seeds, fruits, cuttings, stem tubers, root tubers, shoots, adventitious buds, adventitious embryos, calluses, protoplasts) which can then be used to produce the isoprenoid-producing plant on a large scale.

Techniques to regenerate plants from transgenic plant cells are already known; for example, Doi et al. disclose techniques for eucalyptus (JP 2000-316403 A), Fujimura et al. disclose techniques for rice (Fujimura et al., (1995), Plant Tissue Culture Lett., vol. 2: p 74-), Shillito et al. disclose techniques for corn (Shillito et al., (1989), Bio/Technology, vol. 7: p 581-), Visser et al. disclose techniques for potato (Visser et al., (1989), Theor. Appl. Genet., vol. 78: p 589-), and Akama et al. disclose techniques for *Arabidopsis thaliana* (Akama et al., (1992), Plant Cell Rep., vol. 12: p 7-). Those skilled in the art can regenerate plants from transgenic plant cells according to these documents.

Whether a target transcription factor gene is expressed in a regenerated plant may be determined by well-known methods. For example, western blot analysis may be used to assess the expression of a target transcription factor.

Seeds can be obtained from the transgenic plant, for example, as follows: the transgenic plant is rooted in an appropriate medium and then transplanted to water-containing soil in a pot, and grown under proper cultivation conditions so as to finally produce seeds, which are then collected. Further, plants can be grown from seeds, for example, as follows: seeds obtained from the transgenic plant as described above are sown in water-containing soil, and grown under proper cultivation conditions into plants.

According to the present invention, the isoprenoid-producing plant into which has been introduced a gene encoding a bZIP transcription factor can be used for the production of polyisoprenoids to increase polyisoprenoid production. Specifically, polyisoprenoids can be produced by culturing transgenic plant cells prepared as described above, calluses obtained from such transgenic plant cells, cells redifferentiated from such calluses, or the like in an appropriate medium, or by growing transgenic plants regenerated from the transgenic plant cells, plants grown from seeds collected from such transgenic plants, or the like under proper cultivation conditions. In the isoprenoid-producing plant of the present invention, the rate-limiting step of IPP biosynthesis in the MVA pathway is enhanced by the bZIP transcription factor introduced therein, and therefore the polyisoprenoid biosynthesis pathway is suitably enhanced. Thus, it is possible to suitably increase polyisoprenoid production.

The term "polyisoprenoid" as used herein is a generic term used to refer to polymers having isoprene ($C_5H_8$) units. Examples of polyisoprenoids include polymers such as monoterpenes ($C_{10}$), sesquiterpenes ($C_{15}$), diterpenes ($C_{20}$), sesterterpenes ($C_{25}$), triterpenes ($C_{30}$), tetraterpenes ($C_{40}$), and natural rubber.

As described above, in the present invention, which enables to regulate (enhance) the expression of hydroxymethylglutaryl-CoA reductase by a bZIP transcription factor, the rate-limiting step of IPP biosynthesis in the MVA pathway is enhanced, whereby the polyisoprenoid biosynthesis pathway is suitably enhanced. Thus, it is possible to suitably increase polyisoprenoid production in the transformant.

Moreover, in the isoprenoid-producing plant of the present invention into which has been introduced a gene encoding a bZIP transcription factor, the rate-limiting step of IPP biosynthesis in the MVA pathway is enhanced by the bZIP transcription factor introduced therein, and therefore the polyisoprenoid biosynthesis pathway is suitably enhanced. Accordingly, the use of the isoprenoid-producing plant in the production of polyisoprenoids suitably increases polyisoprenoid production.

As described above, the method of the present invention, the isoprenoid-producing plant of the present invention, and the method of producing a polyisoprenoid of the present invention, which are capable of increasing polyisoprenoid production, can be effective for natural rubber source depletion that is of concern.

EXAMPLES

The present invention will be specifically described by reference to examples. The examples are not to be construed as limiting the present invention.

(Preparation of Promoter Sequence)

A DNA fragment containing the gene encoding HMG-CoA reductase from leaves of *Hevea brasiliensis* (the base sequence of the gene is set forth in the sequence listing as SEQ ID NO: 5) and its promoter was cloned in the following manner. First, genomic DNA was extracted from leaves of *Hevea brasiliensis*. The extraction was carried out using a commercial genomic DNA extraction kit. The gene encoding HMG-CoA reductase with its promoter region was amplified by TAIL-PCR using random primers shown as Primers 1 to 6 and primers corresponding to the gene encoding HMG-CoA reductase.

Primer 1: 5'-ntcgastwtsgwgtt-3' (SEQ ID NO: 7)

Primer 2: 5'-ngtcgtswganawgaa-3' (SEQ ID NO: 8)

Primer 3: 5'-wgtgnagwancanag-3' (SEQ ID NO: 9)

Primer 4: 5'-sttntastnctntgc-3' (SEQ ID NO: 10)

Primer 5: 5'-sstggstanatwatwct-3' (SEQ ID NO: 11)

Primer 6: 5'-agwgnagwancanaga-3' (SEQ ID NO: 12)

The base sequences of the DNA fragments obtained using the primers were analyzed to obtain the promoter sequence of HMG-CoA reductase. The base sequence of the promoter sequence of HMG-CoA reductase is shown as SEQ ID NO: 13.

The promoter sequence was analyzed using a plant promoter database (a database of plant cis-acting regulatory DNA elements (PLACE)) (http://www.dna.affrc.go.jp/PLACE/).

The analysis revealed that the sequence contains a bZIP transcription factor binding (recognition) site (ACACNNG).

(Amplification of Promoter Region)

As the promoter region of the gene, the following regions were amplified by PCR.
HMG-CoA reductase promoter: −1 to −1500 bp, −1 to −1000 bp, −1 to −500 bp The PCR products were each cloned into pMD20T (TAKARA BIO INC.) to construct pMD20T-hmgpro (−1500), pMD20T-hmgpro (−1000), and pMD20T-hmgpro (−500). The inserted PCR products were sequenced to confirm that no mutation was introduced.

(Construction of Reporter Sequence-Containing Vector)

The plasmids constructed in (Amplification of promoter region) were restricted with SpeI and any of HindIII, KpnI and BamHI, and the promoter sequence fragments were individually incorporated at a site of pYES3/CT/LacZ from which the T7 promoter region had been removed, that is, immediately upstream of the lacZ reporter gene to construct pYES3-hmgprolacZ (−1500), pYES3-hmgprolacZ (−1000), and pYES3-hmgpro (−500). Ligation high ver. 2 (TOYOBO) was used for ligation.

(Construction of Vector for Gene Introduction into Yeast Chromosome)

The sequence from the SpeI site to the CYC1 transcription termination signal of each of the plasmids constructed in (Construction of reporter sequence-containing vector) was amplified by PCR, and the resulting fragments were restricted with SalI, SmaI, XbaI or SphI, thereby providing DNA fragments with the promoter sequences each linked to the lacZ gene. In order to allow the obtained DNA fragments to be inserted into a yeast chromosome, the DNA fragments were individually incorporated into pAUR101 DNA (Takara Bio, Inc.) treated with the same restriction enzymes to construct pAUR101-hmgprolacZ (−1500), pAUR101-hmgprolacZ (−1000), and pAUR101-hmgpro (−500). Ligation high ver. 2 was used for ligation as above.

(Acquisition of Transcription Factor Gene)

Next, PCR was performed using an *Arabidopsis thaliana* cDNA library as a template. The PCR produced the following two PCR fragments: At5g24800 (BZIP9) (SEQ ID NO: 1), and At3g58120 (BZIP61) (SEQ ID NO: 3). The obtained PCR products were each cloned into pMD20T to construct pMD20T-BZIP9 and pMD20T-BZIP61. The inserted PCR products were sequenced to confirm that no mutation was introduced.

(Construction of Transcription Factor Expression Vector)

The plasmids constructed in (Acquisition of transcription factor gene) were restricted with SpeI, BamHI, or EcoRV, and the transcription factor genes were individually incorporated downstream of the TEF1 promoter region of p427TEF (COSMO BIO Co., Ltd.) to construct pTEF-BZIP9 and pTEF-BZIP61. Ligation high ver. 2 was used for ligation.

(Transformation of Yeast)

The plasmids constructed in (Construction of vector for gene introduction into yeast chromosome) and (Construction of transcription factor expression vector) were introduced into yeast cells (BY4741 strain) by electroporation. Screening for transgenic yeast cells was carried out by culturing the yeast cells on a medium containing the antifungal antibiotics Aureobasidin A (Takara Bio, Inc.) and G418 (Wako Pure Chemical Industries, Ltd.).

(Demonstration of Effect of Transcription Factor)

The transgenic yeast cells were cultured on a medium containing X-gal to assess the expression of lacZ due to transcription factor activity. Specifically, when the lacZ reporter gene, which is linked to the promoter sequence, is expressed, X-gal in the medium is then decomposed to develop a blue color. Based on this mechanism, if the medium turned blue, it was determined that lacZ was expressed due to transcription factor activity. This test was repeated 10 times. Table 1 shows how many times lacZ was expressed due to transcription factor activity.

TABLE 1

| | Transcription factor | | |
| Promoter sequence | At5g24800 (BZIP9) | At3g58120 (BZIP61) | Control (with no transcription factor) |
| --- | --- | --- | --- |
| hmg (−1500) | 5 | 4 | 1 |
| hmg (−1000) | 4 | 4 | 1 |
| hmg (−500) | 1 | 0 | 0 |

Number of yeast cells that exhibited reporter gene activity (N = 10)

Table 1 shows that the use of At5g24800 (BZIP9) (SEQ ID NOs: 1 and 2), or At3g58120 (BZIP61) (SEQ ID NOs: 3 and 4), particularly At5g24800 (BZIP9), enhanced the reporter gene activity. Further, At5g24800 (BZIP9) and At3g58120 (BZIP61) have proved to function as transcription factors for HMG-CoA reductase because the longer the sequence of the promoter region was, the more often the reporter gene activity was expressed, or, in other words, the larger number of At5g24800 (BZIP9) or At3g58120 (BZIP61)-binding sites the promoter sequence contained, the more often the reporter gene activity was expressed. These results demonstrated that the introduction of At5g24800 (BZIP9) or At3g58120 (BZIP61), particularly At5g24800 (BZIP9), into an isoprenoid-producing plant enhances the rate-limiting step of IPP biosynthesis in the MVA pathway, and thereby suitably enhances the polyisoprenoid biosynthesis pathway, and thus it is possible to suitably increase polyisoprenoid production.

(Sequence Listing Free Text)
SEQ ID NO: 1: base sequence of BZIP9-encoding gene from *Arabidopsis thaliana*
SEQ ID NO: 2: amino acid sequence of BZIP9 from *Arabidopsis thaliana*
SEQ ID NO: 3: base sequence of BZIP61-encoding gene from *Arabidopsis thaliana*
SEQ ID NO: 4: amino acid sequence of BZIP61 from *Arabidopsis thaliana*
SEQ ID NO: 5: base sequence of HMG-CoA reductase-encoding gene from *Hevea brasiliensis*
SEQ ID NO: 6: amino acid sequence of HMG-CoA reductase from *Hevea brasiliensis*
SEQ ID NO: 7: primer 1
SEQ ID NO: 8: primer 2
SEQ ID NO: 9: primer 3
SEQ ID NO: 10: primer 4
SEQ ID NO: 11: primer 5
SEQ ID NO: 12: primer 6
SEQ ID NO: 13: base sequence of promoter sequence of HMG-CoA reductase from *Hevea brasiliensis*

The invention claimed is:

1. A method of regulating the expression of hydroxymethylglutaryl-CoA reductase by a heterologous bZIP transcription factor,
   wherein the method comprises introducing a gene encoding the bZIP transcription factor into a *Hevea* or *Taraxacum* plant to regulate the expression of hydroxymethyglutaryl-CoA reductase in the plant,
   wherein the bZIP transcription factor is any of the following proteins:
   [1] a protein comprising the amino acid sequence of SEQ ID NO: 2; and
   [2] a protein having transcription factor activity and comprising an amino acid sequence that has at least 90% sequence identity to the amino acid sequence of SEQ ID NO: 2.

2. The method according to claim 1,
   wherein the gene is a DNA comprising the base sequence of SEQ ID NO: 1.

3. The method according to claim 1,
   wherein the method enhances the expression of hydroxymethylglutaryl-CoA reductase by the bZIP transcription factor.

4. A *Hevea* or *Taraxacum* plant into which has been introduced a heterologous gene encoding a bZIP transcription factor,
   wherein the gene is a DNA comprising the base sequence of SEQ ID NO: 1.

5. A method of producing a polyisoprenoid comprising growing the isoprenoid-producing plant according to claim 4.

* * * * *